(12) United States Patent
Noerenberg et al.

(10) Patent No.: US 6,909,088 B2
(45) Date of Patent: Jun. 21, 2005

(54) MEASUREMENT METHOD OF THE RATE OF TRANSMISSION OF A VAPOR THROUGH A SAMPLE

(75) Inventors: Holger Noerenberg, Oxford (GB); Andrew Briggs, Oxford (GB); George Smith, Witney (GB); Yusuke Tsukahara, Tokyo (JP); Takashi Miyamoto, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 10/223,470

(22) Filed: Aug. 20, 2002

(65) Prior Publication Data

US 2003/0001086 A1 Jan. 2, 2003

Related U.S. Application Data

(63) Continuation of application No. PCT/JP01/09727, filed on Nov. 7, 2001.

(30) Foreign Application Priority Data

Nov. 9, 2000 (GB) ............................................. 0027431

(51) Int. Cl.⁷ ............................................... H01J 49/00
(52) U.S. Cl. ..................................................... 250/282
(58) Field of Search ........................... 250/282; 204/1 T

(56) References Cited

U.S. PATENT DOCUMENTS

| | | | | | |
|---|---|---|---|---|---|
| 3,926,561 A | * | 12/1975 | Lucero | ........................ | 436/178 |
| 4,050,995 A | * | 9/1977 | Bredeweg | .................... | 205/788 |
| 5,172,583 A | * | 12/1992 | Tallon | ......................... | 73/40.7 |
| 5,889,281 A | * | 3/1999 | Holkeboer et al. | ......... | 250/282 |

* cited by examiner

Primary Examiner—John R. Lee
Assistant Examiner—Phillip A Johnston

(57) ABSTRACT

A method of measuring the rate of transmission of a vapor through a test sample using a mass spectrometer. The test sample is sealed to a gas cell defining a gas chamber, covering an opening in the gas chamber. A droplet of water including isotopes of mass number placed in the gas chamber and the gas cell is introduced into a vacuum chamber adjacent a mass spectrometer. After a sufficient time for evaporation of the liquid to saturate the gas chamber with vapor and for the output of the mass spectrometer to stabilize, the partial pressure of vapor in the vacuum chamber is measured using the mass spectrometer. The measure partial pressure is used to derive the rate of transmission of the vapor through the test sample.

25 Claims, 2 Drawing Sheets

MEASUREMENT METHOD OF THE RATE OF TRANSMISSION OF A VAPOR THROUGH A SAMPLE

CROSS-REFERENCE TO RELATED APPLICATIONS

This application is a continuing application, filed under 35 U.S.C. §111(a), of International Application PCT/JP01/09727, filed Nov. 7, 2001, it being further noted that foreign priority benefit is based upon United Kingdom Patent Application 0027431.6, filed Nov. 9, 2000.

This application is based upon and claims the benefit of priority from the prior United Kingdom Patent Application No. 0027431.6, filed Nov. 9, 2000, the entire contents of which are incorporated herein by reference.

BACKGROUND OF THE INVENTION

1. Field of the Invention

The present invention relates to measurement method of the rate of transmission of a vapor through a sample, such as a film of a polymer, a ceramic or a composite or a biological sample.

2. Description of the Related Art

Understanding of the transmission of gasses and vapors through materials of great importance in many fields, for example in medicine, food packaging and for chemical separation processes. Various techniques for measuring the rate of transmission of gasses and through a film are known. Some techniques are based on electrochemical principles, others use a sensor such as a modulated infra-red (IR) sensor. Other techniques measure the pressure increase caused by permeating gasses or vapors, for example using an ion gauge or a PIRANI gauge.

For example, a common known device for measuring rates of transmission of water vapor is the device sold under the Trade Mark PERMATRAN, which uses a modulated IR sensor. This known device uses samples having an area of the order of 100 cm$^2$ and has a practical resolution of around 5 mg/m$^2$/day. However, it would be desirable to obtain a greater sensitivity to allow the measurement of lower absolute rates of transmission of vapor. This would allow, for example, the study of samples with a given transmission rate per unit area having a smaller effective area or samples having a lower transmission rate per unit area, than is possible with the known IR sensor devices.

It is also known to measure the rate of transmission of various gases through a sample using a mass spectrometer to measure the partial pressure of the various species of gas molecule transmitted from a gas chamber through the sample into a vacuum chamber under vacuum. In some known mass spectrometer techniques, the partial pressure in the vacuum chamber decays exponentially over time. This creates difficulties in measuring gas transmission rates, because of difficulties in both (i) modeling the decay to relate the decay to a transmission rate, and (ii) accurately extracting the decay co-efficient from the data, especially at low absolute transmission rates. This is a particular problem for larger molecules which exhibit exponential behavior, that is the measured particular pressure is the sum of two different exponential decay curves having a different magnitudes and time constants. This even further complicates any model used to extract coefficients.

There are also known mass spectrometer techniques in which the test sample is fixed in the apparatus separating the gas chamber from the vacuum chamber and the gas chamber is supplied with gas at a constant pressure from an external source. However, such an apparatus presents a number of practical difficulties. It is necessary to have a pressurized source of the gas. It is cumbersome to change the test sample. Also, it is impractical to use the apparatus at Ultra High Vacuum, because the evacuation process including baking risks damage or destruction of the test sample. Consequently the sensitivity to low absolute transmission rates is reduced because the background measurements are high.

BRIEF SUMMARY OF THE INVENTION

The present invention is intended to provide a method of measuring the rate of transmission of vapors, such as water vapor through a test sample that alleviates the problems with the known techniques discussed above.

According to a first embodiment of the present invention, there is provided a method of measuring the rate of transmission of a vapor through a test sample, comprising:

providing an amount of liquid in a gas chamber;

arranging the gas chamber to communicate through a test sample with a vacuum chamber under vacuum;

using a mass spectrometer to measure the partial pressure in the vacuum chamber of the vapor of the liquid after a sufficient time for evaporation of the liquid to saturate the gas chamber with vapor; and deriving the rate of transmission of the vapor through the test sample from the measured partial pressure.

With the first embodiment of the present invention, the use of a mass spectrometer provides increased sensitivity as compared to the known IR sensor techniques, thereby allowing measurement of a lower absolute gas transmission rate. This allows study of, for example, samples having a lower gas transmission rate per unit area or samples with a given gas transmission rate per unit area of smaller area, as compared to the IR sensor techniques.

In addition, in the first embodiment of the present invention, there are advantages in generating the vapor by providing an amount of liquid in a gas chamber. The liquid evaporates to fill the gas chamber with vapor. After a time, the vapor saturates the gas chamber. Once saturated, the vapor in the gas chamber will remain at a constant pressure, namely the vapor pressure of the liquid. Consequently, after saturation of the gas chamber, the rate of transmission through the test sample into the vacuum chamber occurs at a constant rate and consequently the partial pressure measured by the mass spectrometer is also a constant value. This simplifies measurement and calibration of the measured partial pressure to derive the rate of transmission. In particular, this represents an improvement over the known techniques where the mass spectrometer measures a partial pressure that decays exponentially. Furthermore, the generation of a vapor in the gas chamber by the provision by an amount of liquid provides the advantage of great simplicity as compared to the known techniques using an external gas source.

Advantageously, the gas chamber is formed in a gas cell having an opening, the test sample being sealed to the gas cell covering the opening, and the step of arranging the gas chamber to communicate through the test sample with the vacuum chamber comprises introducing the gas cell into the vacuum chamber.

This provides a number of advantages. The gas cell may be easily filled outside the vacuum chamber. A succession of measurements for different samples and/or different vapors may be performed by introducing successive gas cells into the vacuum chamber without the need to re-establish the vacuum for each measurement. The temperature of the gas cell may be easily changed without the need to change the temperature of the entire apparatus including the vacuum chamber, thereby allowing study of the change in transmission rate with temperature.

According to a second embodiment of the present invention, there is provided a method of measuring the rate of transmission of water vapor through a test sample, comprising:

arranging a gas chamber containing water vapor including isotopes of mass number 20 to communicate through a test sample with a vacuum chamber under vacuum;

using a mass spectrometer to measure the partial pressure of isotopes of mass number 20 of water vapor in the vacuum chamber; and deriving the rate of transmission of water vapor through the test sample from the measured partial pressure.

With the second embodiment of the present invention, by measuring the partial pressure of isotopes of water vapor of mass number 20, it is possible to achieve a high degree of sensitivity. This allows measurement of lower absolute gas transmission rates than is possible by measuring the partial pressure of ordinary water of mass number 18. This is because the background pressure within the vacuum chamber is much lower for water of mass number 20 than for water of mass number 18, because naturally occurring water of mass number 20 is in far less abundance. Therefore, lower amounts of transmitted vapor can be distinguished against the background.

A method that embodies the present invention will now be described by way of non-limitative example. The method embodies both aspects of the present invention that may be combined together. The method is described with reference to the accompanying drawings.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention in which.

DETAILED DESCRIPTION OF THE INVENTION

Embodiments according to the present invention will now be described with reference to the accompanying drawings.

Figure 1:
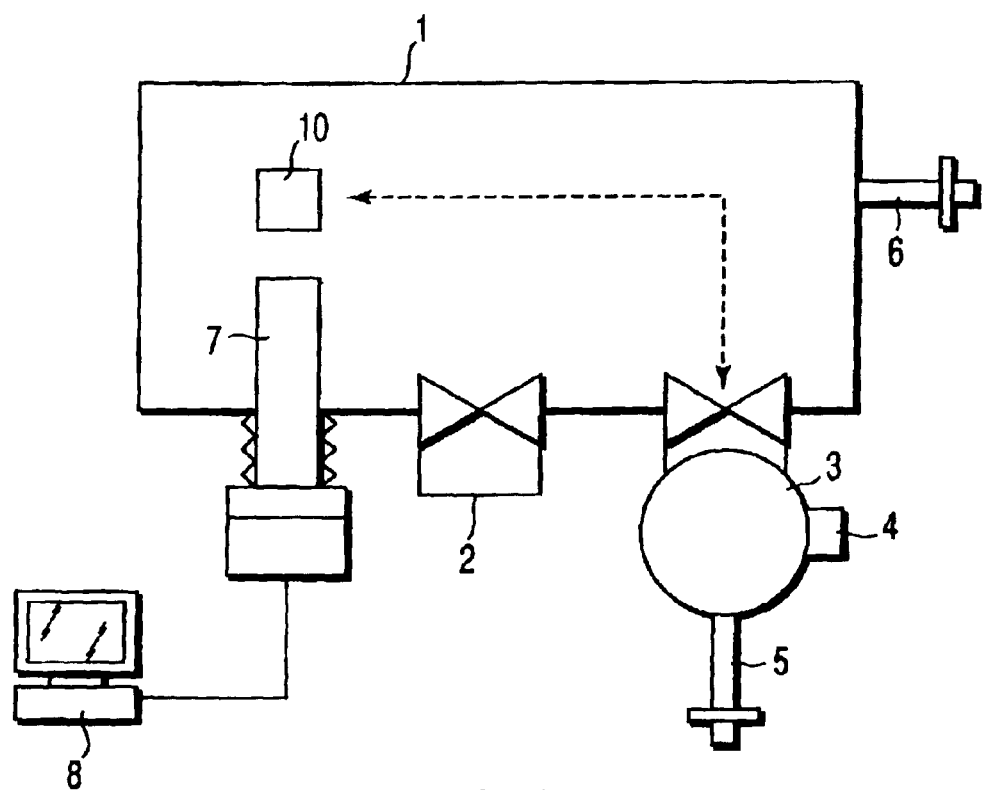
FIG. 1 is a diagrammatic view of the apparatus used in the method.

The method is performed using the apparatus illustrated in diagrammatic from in FIG. 1.

The apparatus includes a standard vacuum chamber 1 capable of withstanding Ultra High Vacuum (UHV). The vacuum chamber 1 is pumped by a main turbo-molecular pump 2. The vacuum chamber 1 has a load lock chamber 3 acting as an air lock in a conventional manner and pumped by a further turbo-molecular pump 4. The vacuum chamber 1 has two transfer arms 5, 6. The first transfer arm 5 is arranged to transfer objects through the load lock chamber 4. The second transfer arm 6 is arranged to transfer objects introduced by the first transfer arm 5 through the load lock chamber 3.

Disposed within the vacuum chamber 1 is a quadrupole mass spectrometer 7 arranged to detect vapor in the vacuum chamber 1. The mass spectrometer 7 is of conventional construction having an SEM detector. Any type of mass spectrometer could be used, although a quadrupole mass spectrometer is preferred because its relatively small size assists mounting in the vacuum chamber 1. The sensitivity of the method can be improved by using a mass spectrometer of higher sensitivity.

The output of the mass spectrometer 7 is fed to a conventional personal computer 8 for data processing.

The apparatus further includes a gas cell 10 of a sufficiently small size to be introduced into, and removed from, the vacuum chamber 1 through the load lock chamber 3. The gas cell 10 may be moved using the two transfer arms 5, 6 to a position adjacent the mass spectrometer 7.

Figure 2:
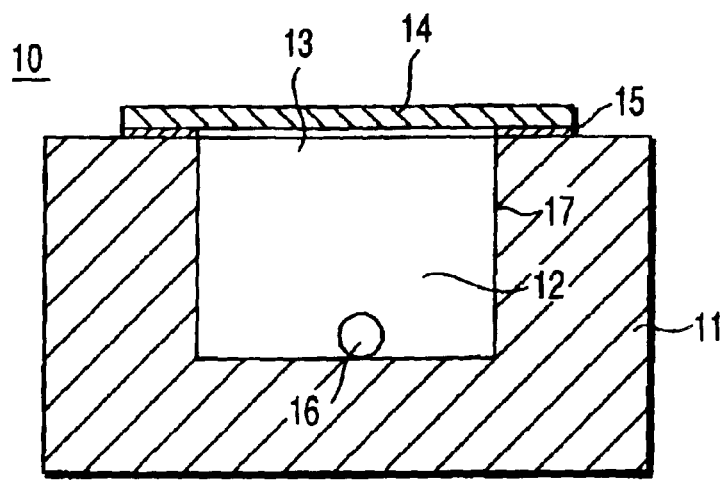
FIG. 2 is a cross-sectional view of a gas cell used in the method.

The gas cell 10 is illustrated in cross-section in FIG. 2. The gas cell 10 is formed from a stainless steel body 11 having a cylindrical hole 17 drilled therein to form a gas chamber 12 with an opening 13. A test sample 14 covers the opening 13 and is sealed to the block 11 by an adhesive 15.

The gas cell 10 is filled before the sample 14 is sealed to the block 11 by placing a droplet 16 of liquid into the gas chamber 12. Subsequently the sample 14 is sealed to the block 11. The area of the opening 13 is the effective area of the sample 14 for transmission of gas. The effective area may be of any size. However, it is easy to form the gas cell 10 to provide low effective areas, of say around 1 cm$^2$ or less. This compares favorably with the PERMATRAN device mentioned above which uses samples having an area of the order of 100 cm$^2$.

The present invention is particularly suitable for a sample 14 consisting of a thin film, for example of a polymer, a ceramic or a composite. In this case, the sample 14 is sufficiently thin that transmission through its minor edges is negligible compared to transmission through its major faces extending across the opening 13. In this case, the measured rate of transmission of vapor may be expressed as a rate per unit area of the sample 14. The present invention is also suitable for a sample 14 that is a biological sample.

The method for measuring the rate of transmission of vapor through the sample 14 using the apparatus described above will now be described.

Initially, the vacuum chamber 1 is evacuated to UHV, typically at a pressure of the order of $10^{-8}$ Pa or below, using known techniques involving pumping and baking of the vacuum chamber 1. Subsequently, the vacuum chamber 1 is maintained at UHV by the turbo-molecular pump 2. The evacuation process is performed while the gas cell 10 is disposed outside the vacuum chamber 1. This prevents the evacuation process, in particular the baking, from damaging the sample 14.

Outside the vacuum chamber 1, the gas cell is filled by placing a droplet of liquid 16 into the chamber 12. The chamber 12 is sufficiently deep that the droplet of liquid 16 does not lie in opening 13 or contact the sample 14. Then the sample 14 is sealed to the block 11 by the adhesive 15.

The filled gas cell 10 is introduced into the vacuum chamber 1 using the two transfer arms 5, 6. The gas cell 10 is positioned opposite the mass spectrometer 7 with the sample 14 a few millimeters or closer, say 0.5 mm, from the entrance of the mass spectrometer 7 which may be an aperture of, say, 1 mm diameter in a metallic plate. As a result, the gas chamber 12 communicates with the vacuum chamber 1 through the sample 14. Vapor transmitted through the sample 14 is detected by the mass spectrometer 7 which outputs, in respect of each mass number (or strictly speaking the charge-to-mass ratio), a signal representative of the partial pressure of the corresponding constituent of the vapor in the vacuum chamber 1. The output signal is analyzed on the personal computer 8.

The liquid in the gas cell 10 evaporates to form vapor in the gas chamber 12. After a sufficient period of time, the vapor saturates the gas chamber 12. Thereafter, the pressure in the gas chamber 12 remains at a constant value, namely the vapor pressure of the liquid until all the liquid in the droplet 16 has evaporated.

After insertion of the gas cell 10 into the vacuum chamber 1, the output of the mass spectrometer 7 in respect of each constituent of the liquid rises from the background level for that species. Eventually it stabilizes at a constant value. Typically this takes several hours. In this state, the system is in equilibrium with the vapor in the gas chamber 12 at a constant pressure being transmitted through the sample 14 at a constant rate. The partial pressure for each constituent measured by the mass spectrometer 7 is proportional to the gas transmission rate of that constituent. Therefore, a measurement of the partial pressure is taken during this stable period of the output of the mass spectrometer 7.

The equilibrium remains until all the liquid in the droplet 16 has evaporated (or the gas cell 10 is removed from the vacuum chamber 12, if sooner). After that, the pressure in the chamber 12 decays exponentially as vapor is transmitted out of the chamber 12 without being replaced. This causes a corresponding decay in the rate of transmission and the output of the mass spectrometer 7.

The measured partial pressures are used to derive the rate of transmission of the vapor through the sample 14. This is done by calibrating the measurement of partial pressure for a sample 14 constituting a test sample against of partial pressure measured for a further sample 14 constituting a reference sample. The reference sample has 9 rate of transmission of the vapor that is known, for example from another technique. The partial pressure measurements for the test sample and the reference sample may both be obtained using the same method, as described herein. Alternatively, the rate of transmission could be derived from the measured partial pressure based on a theoretical analysis of the transmission.

The measurements of partial pressure and derived rates of transmission may be considered for individual constituents of the vapor or for all the constituents of the vapor in summation.

As the measurement of partial pressure is taken during the stable equilibrium state of the apparatus, it is particularly easy to take an accurate measurement and to derive the rate of transmission. In particular, this is easier than in techniques where the partial pressure measured by a mass spectrometer decays exponentially.

Furthermore, the present invention provides significant advantages of simplicity. The gas cell 10 may be filled outside the vacuum chamber 1. Furthermore, the method may be repeated for different samples 14 and/or different vapors simply by replacing one gas cell 10 with another without the need to evacuate the vacuum chamber 1 each time, although throughput is limited by the time taken to restore the background level of the vapor in the vacuum chamber 1 after an experiment.

The method may be repeated for a given sample and a given vapor at different temperatures to investigate changes in the rate of transmission with temperature and hence derive the activation energy of the sample 14. It is easy to change the temperature of the gas cell 10, using any known technique, because it is only necessary to change the temperature of the gas cell 10, not the vacuum chamber 1 as a whole. The temperature of the gas cell 10 may be measured using a thermocouple.

The present method may be used to measure the rate of transmission of any vapor, but is particularly suitable for measuring the rate of transmission of water vapor. In this case, to enhance sensitivity, the partial pressure of isotopes of water of mass number 20 may be measured by using a droplet 16 of liquid water that includes, or consists essentially of, isotopes of mass number 20. The background pressure within the vacuum chamber for water of mass number 20 is less than for water of mass number 18 because naturally occurring water of mass number 20 is in far less abundance. Therefore, the use of water of mass number 20 allows lower measurements of partial pressure corresponding to lower transmission rates to be measured without being obscured by the background pressure. In the described embodiment the personal computer 8 in its analysis of the output of the mass spectrometer 7 derives the ratios of transmission and so effectively selects the partial pressure of isotopes of mass number 20.

Water of mass number 20 can be comprised of oxygen of mass number 18 (0.2% natural abundance) instead of 16 or by using hydrogen of mass number 2 (0.015% natural abundance) instead of 1. Either source of water of mass number 20 may be used.

Figure 3:
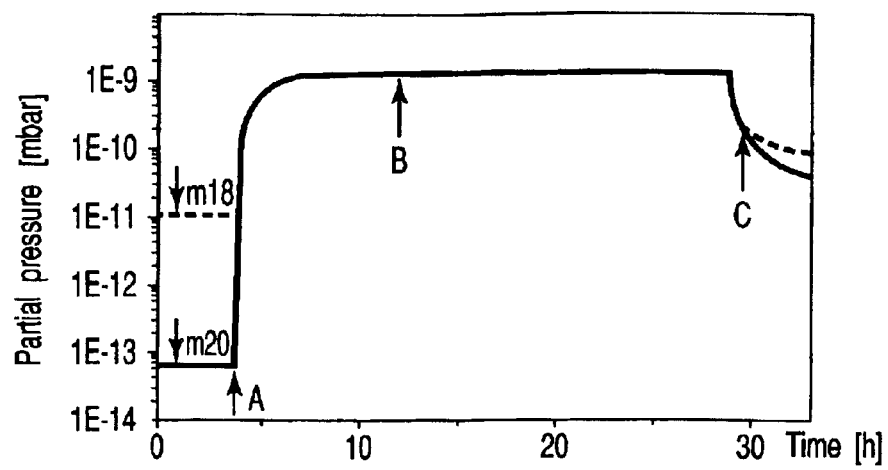
FIG. 3 is a graph showing an example of results obtained with the method.

To illustrate its effectiveness, an example of measurements obtained using the present method are illustrated in FIG. 3. These measurements were obtained for a sample 14 consisting of a film of oriented polypropylene (OPP) of thickness 20 $\mu$m and having effective area of 0.126 cm$^2$. The liquid used was water including isotopes of mass number 20. In fact the experimental results show that the water contained approximately equal amounts of isotopes of mass number 20 and isotopes of mass number 18. FIG. 3 is a graph of the measured partial pressure for each isotope of water against time. The measurements for mass number 20 are shown by the dark line and the measurements for mass number 18 are shown by the fainter line.

The gas cell 10 was introduced into the vacuum chamber 1 after four hours on the time scale at the position A. Prior to this, the partial pressures readings output by the mass spectrometer 7 are the background pressures. It will be seen that the background pressure is much lower for mass number 20, than for mass number 18. This is because the background pressure in the vacuum chamber 1 at UHV is formed in part by naturally occurring water which contains an abundance of water of mass number 20 at several orders of magnitude below that of water of mass number 18.

After the gas cell 10 is introduced into the vacuum chamber 1 at position A, the partial pressure of both isotopes of water rise, stabilizing at a constant value at position B. This is where the measurement of partial pressure is taken.

The stable partial pressure is maintained for a period of time. At position C the gas cell was removed from the vacuum chamber 1. Subsequently the output of the mass spectrometer 7 decayed exponentially down to background levels.

In fact, the partial pressure for each species of water was around $1 \times 10^{-9}$ mbar. Therefore, the total pressure for the transmitted water vapor is $2 \times 10^{-9}$ mbar. In the present case, this calibrates the apparatus, because the sample 14 of OPP has a known rate of transmission of approximately 3 g/m²/day as measured by the PERMATRAN device as discussed above.

If water consisting solely of isotopes of mass number 18 were used, this gives a theoretical lower detection limit of roughly 0.1 mg/m²/day for the sample 14 having an effective area of 0.126 cm². In practice, this lowermost detection limit will probably not be achievable because of problems such as achieving a sufficient seal, but the achievable sensitivity to low absolute rates of transmission compares favorably with the PERMATRAN device which uses samples having an area of the order of 100 cm² and has a lower detection limit of around 5 mg/m²/day. The sensitivity of the techniques to absolute detection rate may be compared by multiplying the lower detection limit of the measurable rate of detection per unit area by the size of the sample used. It is expected that the present method could achieve a sensitivity to low absolute detection rates as compared to the PERMATRAN device around three orders of magnitude better, if water of mass number 20 is used. Such higher sensitivity to low transmission rates is advantageous. It allows, for example, the study smaller samples being a given transmission rate per unit area or of samples having a low transmission rate per unit area.

The experiments described above were performed with a quadrapole mass spectrometer 7 having 6 mm rods in analogue mode. Another order of magnitude in the detection range can be obtained if larger rods, say of 9 mm or 12 mm, were used. Signal detection may also be improved by improving existing amplifiers or using new amplifiers and using pulse counting techniques.

Of course, various modifications may be made to method described above without department from the scope of the present invention. For example the method steps may be performed in a different order or a different apparatus may be used. In particular, the gas cell 10 may be replaced by a gas cell of an alternative construction.

Figure 4:
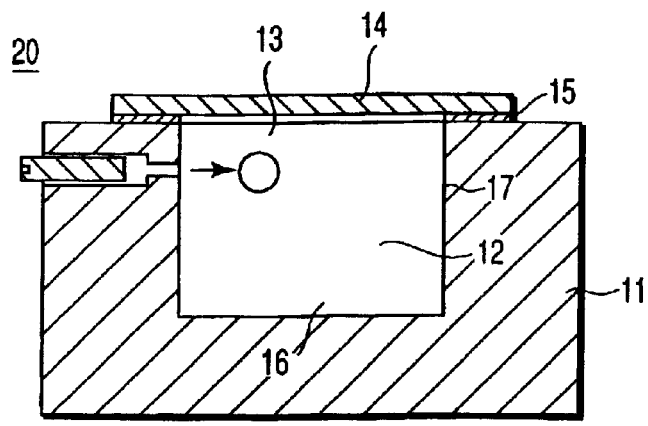
FIG. 4 is a cross-sectional view of a first alternative gas cell.

FIG. 4 illustrates a gas cell 20 having a first alternative construction. The gas cell 20 of FIG. 3 has in most part an identical construction to the gas cell 10 of FIG. 2 (so a description is not repeated), except for the provision of a refill port 21. The refill port 21 is a bore drilled through the block 11 into the gas chamber 12 and formed with an internal thread 22. To close the refill port 21, a cylindrical, externally threaded copper plug 23 is screwed into the internal thread 22 of the port 21. The plug 23 is removable to allow filling of the gas chamber 12 through the refill port 21 to insert a droplet 24 of liquid. Subsequently the plug 23 is screwed back into the thread 22 to close the refill port 21.

The refill port 21 allows the gas chamber 12 of the gas cell 20 to be refilled without the need to remove the sample 14 and re-seal it to the block 11, as is necessary with the gas cell 10 of FIG. 1. This provides the possibility of refilling the gas cell 20 when in the vacuum chamber 1 or in another vacuum chamber which is desirable if the vapor is hazardous or to prevent harm to the vacuum in the vacuum chamber.

The use of closable refill port such as the refill port 21 in the gas cell 20 of FIG. 4 also has the advantages of permitting the gas chamber 12 to be filled with vapor at a temperature above boiling point, which is condensed to a smaller amount of liquid at a lower investigation temperature. It also allows the introduction of a solid at a lower temperature that is investigated at a higher temperature above its melting point to provide liquid in the vacuum chamber.

Figure 5:
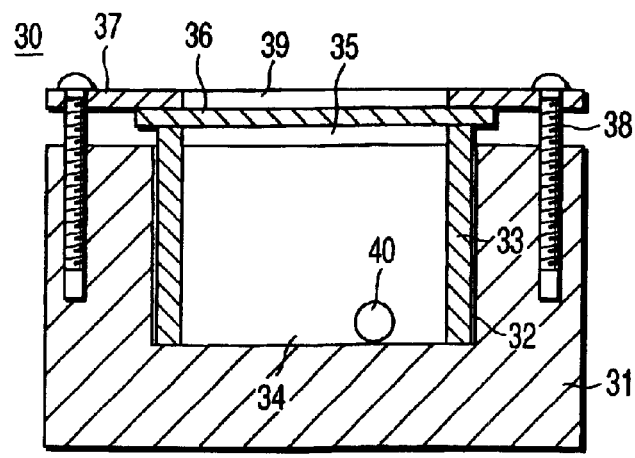
FIG. 5 is a cross-sectional view of a second alternative gas cell.

FIG. 5 illustrates a gas cell 30 having a second alternative construction. The gas cell 30 is formed from a stainless steel block 31 having a cylindrical hole 32 drilled therein. An annular Teflon seal 33 is inserted into the hole 32 to form, inside the annulus of the seal 33, a gas chamber 34 having an opening 35. The sample 36 is positioned on the end of the seal 33 to cover the opening 35. The sample 36 is sealed by the clamping action of an annular lid 32 positioned across the sample and secured to the body 31 by screws 38. The lid 37 has a circular aperture 39 having the same shape as, and aligned with, the opening 35. The area of the opening 35 and the aperture 39 define the effective area of the sample 36. The gas cell 30 is filled by removing the sample 36 and lid 37, placing a droplet 40 of liquid in the chamber 34 and clamping the sample 36 over the chamber 34 using the lid 37 and screws 38.

In any case cells 10, 20 or 30, the sample 14 may be reinforced by a metal grid (not shown) similar to those used in electron microscopy to prevent bulging due to the one atmosphere pressure differential between the vacuum chamber 1 and the gas chamber 12 or 34.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of measuring a rate of transmission of water vapor through a test sample, comprising:

arranging a gas chamber containing the water vapor including isotopes of mass number 20 to communicate through a test sample with a vacuum chamber under vacuum;

using a mass spectrometer to measure a partial pressure of the isotopes of mass number 20 of water vapor in the vacuum chamber;

measuring the partial pressure of the isotopes of mass number 20 of water vapor in the vacuum chamber raised from a background level of the isotopes; and deriving the rate of transmission of water vapor through the test sample from the measured partial pressure which is raised from the background level of the isotopes, wherein the gas chamber is formed in a gas cell having an opening with the test sample sealed to the gas cell covering the opening, the arranging of the gas chamber to communicate through the test sample with the vacuum chamber comprising introducing the gas cell into the vacuum chamber and water vapor is introduced into the gas cell before the introducing of the gas cell into the vacuum chamber.

2. The method according to claim 1, wherein the test sample is sealed to the gas bell by adhesive.

3. The method according to claim 1, wherein the test sample is sealed to the gas cell by clamping.

4. The method according to claim 1, wherein the gas cell has a closable refill port.

5. The method according to claim 1, wherein the vacuum chamber is under Ultra High Vacuum.

6. The method according to claim 1, wherein the effective area of the test sample is around 1 cm$^2$ or less.

7. The method according to claim 1, wherein the test sample is a film.

8. The method according to claim 7, wherein the film is polymer, a ceramic or a composite.

9. The method according to claim 1, wherein the step of using a mass spectrometer to measure the partial pressure of isotopes of mass number 20 in the vacuum chamber is performed after the output of the mass spectrometer stabilizes to a constant value.

10. The method according to claim 1, wherein the rate of transmission of water vapor through the test sample is derived from the measured partial pressure by calibrating the measured partial pressure with a partial pressure measured for a reference sample having a known rate of transmission of water vapor.

11. An apparatus for measuring a rate of transmission of water vapor, the apparatus comprising:
  a vacuum chamber;
  a test sample;
  a gas chamber provided in the vacuum chamber, the gas chamber having an opening for transmitting gas through the test sample;
  a mass spectrometer for measuring a partial pressure of isotopes of the water vapor of mass numbers 18 and 20 in the vacuum chamber; and
  means for selecting the partial pressure of the isotopes of water vapor of mass number 20 to derive the rate of transmission of water vapor through the test sample, which is raised from a background level of the isotopes of mass number 20 of water vapor in the vacuum chamber
  wherein the gas chamber is formed in a gas cell having the opening, with the test sample sealed to the gas cell covering the opening, the gas chamber to communicate through the test sample with the vacuum chamber and to introduce the gas cell into the vacuum chamber and to introduce into the gas cell before the introducing of the gas cell into the vacuum chamber.

12. The apparatus according to claim 11, further comprising an amount of liquid water in the gas chamber, whereby evaporation of the liquid saturates the gas chamber with vapor.

13. The apparatus according to claim 12, wherein the gas chamber is formed in a gas cell which is removable from the vacuum chamber.

14. The apparatus according to claim 13, wherein the test sample is sealed to the gas cell covering the opening.

15. The apparatus according to claim 14, wherein the test sample is sealed to the gas cell by adhesive.

16. The apparatus according to claim 15, wherein the test sample is sealed to the gas cell by clamping.

17. The apparatus according to claim 11, wherein the gas cell has a closable refill port.

18. The apparatus according to claim 11, wherein the vacuum chamber is under Ultra High Vacuum.

19. The apparatus according to claim 11, wherein the effective area of the test sample is around 1 cm$^2$ or less.

20. The apparatus according to claim 11, wherein the test sample is a film.

21. The apparatus according to claim 20, wherein the film is a polymer, a ceramic or a composite.

22. The apparatus according to claim 11, wherein the selecting means is arranged to select the partial pressure after the output of the mass spectrometer stabilizes to a constant value.

23. The apparatus according to claim 11, further comprising means for deriving the rate of transmission of the vapor through the test sample.

24. The apparatus according to claim 23, wherein the deriving means is arranged to derive the rate of transmission by calibrating the measured partial pressure with a partial pressure measured for a reference sample having a known rate of transmission of the vapor.

25. An apparatus comprising:
  a vacuum chamber;
  a test sample to pass water vapor to the vacuum chamber therethrough;
  a gas cell introduced into the vacuum chamber;
  a unit to measure a partial pressure of isotopes of the water vapor in the vacuum chamber having mass numbers of 18 and 20; and
  a selecting unit to select the partial pressure of the isotopes of the water vapor of mass number 20 to derive a rate of transmission of the water vapor through the test sample to the vacuum chamber, which is raised from a background level of the isotopes of mass number 20 of water vapor in the vacuum chamber;
  the gas cell being filled prior to being introduced into the vacuum chamber.

* * * * *

UNITED STATES PATENT AND TRADEMARK OFFICE
CERTIFICATE OF CORRECTION

PATENT NO.      : 6,909,088 B2
APPLICATION NO. : 10/223470
DATED           : June 21, 2005
INVENTOR(S)     : Holger Noerenberg et al.

It is certified that error appears in the above-identified patent and that said Letters Patent is hereby corrected as shown below:

Column 8, Line 67, delete "bell" and insert -- cell -- therefor.
Column 9, Line 11, after "film is" insert -- a --.

Signed and Sealed this

Thirtieth Day of January, 2007

JON W. DUDAS
*Director of the United States Patent and Trademark Office*